(12) United States Patent
Watanabe et al.

(10) Patent No.: US 6,453,243 B1
(45) Date of Patent: Sep. 17, 2002

(54) METHOD FOR DISPLAYING RESULT OF HYBRIDIZATION EXPERIMENT USING BIOCHIP AND METHOD FOR EVALUATING EXPERIMENTAL ERROR OF HYBRIDIZATION EXPERIMENT

(75) Inventors: Tsunehiko Watanabe; Yasuyuki Nozaki; Ryo Nakashige; Takuro Tamura, all of Kanagawa (JP)

(73) Assignee: Hitachi Software Engineering Co, Ltd., Yokohama (JP)

( * ) Notice: Subject to any disclaimer, the term of this patent is extended or adjusted under 35 U.S.C. 154(b) by 0 days.

(21) Appl. No.: 09/884,833

(22) Filed: Jun. 18, 2001

(30) Foreign Application Priority Data

Sep. 1, 2000 (JP) ........................................ 2000/265933

(51) Int. Cl.$^7$ .......................... C12Q 1/68; C12P 19/34; C07H 21/02; G01N 33/48
(52) U.S. Cl. ............................. 702/19; 435/6; 435/91.1; 536/23.1
(58) Field of Search ................... 435/6, 91.1; 536/23.1; 702/19

(56) References Cited

U.S. PATENT DOCUMENTS

2002/0012940 A1 * 1/2002 Lockhart et al. ................ 435/6

* cited by examiner

*Primary Examiner*—John S. Brusca
*Assistant Examiner*—Young Kim
(74) *Attorney, Agent, or Firm*—Pillsbury Winthrop LLP; John R. Wetherell, Jr.

(57) ABSTRACT

A method for displaying results of hybridization experiments using a biochip is provided. In the method, a plurality of control spots spotted in each of a plurality of sections defined on a biochip is measured. The measured data are plotted on a graph for each section, and all of the graphs are simultaneously displayed on a single screen in the same arrangement as that of the sections on the biochip. By simultaneously displaying all of the graphs on a single screen, it is possible to skim the whole biochip to find experimental errors. Also, experimental errors can be quantified with respect to the dispersion of control data on the basis of the linearity of the data points and slope angles defined for each data points on a graph.

6 Claims, 17 Drawing Sheets

Fig. 2

| Gene ID | Experiment | |
|---|---|---|
| | Normal cell A | Diseased cell B |
| 1 | 1,234 | 56 |
| 2 | 11,224 | 888 |
| 3 | 107 | 3,408 |
| ⋮ | ⋮ | ⋮ |
| m | 9,753 | 8,905 | example  ■ : maximum slope angle   ♦ : average slope angle   ▲ : minimum slope angle

METHOD FOR DISPLAYING RESULT OF HYBRIDIZATION EXPERIMENT USING BIOCHIP AND METHOD FOR EVALUATING EXPERIMENTAL ERROR OF HYBRIDIZATION EXPERIMENT

PRIORITY INFORMATION

This application claims priority to Japanese Application Serial No. 265933/2000, filed Sep. 1, 2000.

BACKGROUND OF THE INVENTION

1. Field of the Invention

The present invention relates to display and evaluation of gene expression data that are obtained by hybridizing genes to a particular gene with known identity. The present invention also relates to a method for displaying and evaluating failures, or errors, occurring in experimental processes for obtaining such data in a manner that is visually easy to interpret.

2. Description of the Related Art

As the number of biological species increases whose genome have been sequenced, genome comparison analyses have become widely used to find genes that evidence evolution of species and search for gene populations that are common among different species. Gene comparison is also employed to find any clues from the differences between species to identify characteristics specific to a particular species.

Due to the recent developments of technological infrastructures such as biochips or DNA chips (which are referred to as "biochips," hereinafter), the subject of interest in molecular biology have been shifting from interspecific information to intraspecific information, namely, simultaneous expression analyses. This type of information, together with conventional interspecific comparisons, widens the possibility of the art from merely extracting information to associating pieces of the information with each other.

For example, if an unknown gene is found to have an expression pattern identical to that of a known gene, it is inferred that the unknown gene has a similar function to the known gene. Functions of these genes and the resulting proteins are studied by considering them as a functional unit or group. Further, how genes or proteins interact with each other is analyzed by associating them with the data for a known enzyme reaction or metabolism, or more directly, by making a gene deficit to terminate the expression of the gene or by making the gene excessively active to permit the overexpression and studying direct or indirect influences of the gene on expression patterns of the entire genes.

In studies of gene expression patterns using biochips, elements that are associated with living tissue of interest are prepared. The term "elements" herein refers to fragments of any DNA that are related to the living tissue of interest. In a biochip, the elements are spotted and immobilized on a substrate such as a slide glass or a silicon wafer with a density of several hundred to several thousand elements per square centimeter. The term "sample" herein refers to fragments of any DNA or RNA that are extracted from living tissue of interest to be reacted with the elements on a biochip. When a gene is expressed in cells, DNA is transcribed into RNA. The RNA is extracted and labeled with a fluorescent marker to serve as a sample. When a sample is reacted with an element, single strands that are complementary to each other bind, or hybridize, to one another. Thus, biochips permit quantitative or qualitative analyses of gene expressions in living tissue by taking advantage of hybridization.

A successful example in the art is the experiment conducted by University of Tokyo, Institute of Medical Science with regard to drug efficacy (T. Tsunoda et al.: Discrimination of Drug Sensitivity of Cancer Using cDNA Microarray and Multivariate Statistical Analysis: Genome informatics 1999 (December 1999) pp.227–228, Universal Academy Press Inc.). In this experiment, RNA extracted from normal cells and RNA extracted from cancer cells are each labeled with a fluorescent dye of different colors. The two types of RNA were mixed and allowed to hybridize to elements (i.e., genes) on a biochip. The intensities of fluorescent signals emitted from each of the two fluorescent dyes were measured.

FIG. 16 schematically shows the manner in which the state of each gene expression that has been obtained from the above-described experiment is displayed. In this manner of display, the data for fluorescent signals resulting from hybridization with genes immobilized on a biochip are plotted on a graph, with one axis representing the fluorescent signals for normal cells and the other representing the signals for cancer cells. One point in the graph corresponds to one gene. In analyzing data, among genes that emit fluorescent signals with higher intensities than a predetermined value, those that are specific to disease conditions are discriminated against the other genes on the basis of the ratio of the signal intensity for the normal cells to the signal intensity for the cancer cells. Specifically, genes corresponding to the points in the area A (i.e., genes that function in normal cells but not in cancer cells) and genes corresponding to the points in the area B (i.e., genes that function in cancer cells but not in normal cells) in FIG. 16 are particularly distinguished. In this manner of displaying data, genes that function specifically in a specific disease can be discriminated.

The data used in such data analysis must be sufficiently reliable in itself to ensure feasibility of the analysis. In other words, the results should be reproducible in experiments conducted under the same conditions. However, the actual manufacturing technologies of biochips, as well as the techniques required for conducting experiments using biochips, are yet to be fully developed, and the reproducibility of experiments is not fully ensured. Underlying causes for this include the difficulty in spotting exactly equal amounts of elements on a biochip and the susceptibility of the technology to changes in environmental factors such as temperatures and humidity. Furthermore, the techniques have not been fully established to ensure constant hybridization reaction rates and the accuracy of the readings of fluorescent light after hybridization. At present, there is a considerable uncertainty concerning the reliability of the data obtained from these experiments.

FIG. 17 schematically shows an image data obtained when the results of a biochip experiment are read by a scanner. Until now, researchers have needed to visually examine such read images of biochips to determine if the data are usable or not. For example, data for a biochip is determined to be unusable when the read image data is dark throughout it (i.e., no expression is observed.), or when the image is partially bright (i.e., incomplete expression). These conditions seem to occur such as when hybridization is incomplete or when the substrate of the biochip is scratched or when spotted amounts on the biochip are not uniform throughout the biochip, though the exact causes are not known.

At present, from manufacturers' point of view, there is an increasing need for technologies to improve the accuracy of manufacturing processes of biochips and to enable mass production of reliable biochips with decreased errors. Thus, proper evaluation methods or tools are needed to accurately determine the accuracy and errors in the manufacturing of biochips. In contrast, from the researchers' point of view who use the biochip in their experiments, it will be convenient if proper evaluation methods or tools are provided for evaluating the results of biochip experiments in order to allow the user to determine if the results are usable or not, and if not, allow the user to find out the exact cause of it. Thus, a need exists for evaluation methods that enable the user to know what faulty events have taken place at what point of the manufacturing process of biochips and/or experiments using biochips and take into account the results in the later manufacturing or experiments.

SUMMARY OF THE INVENTION

The present invention addresses such a need of both of biochip manufacturers and users. Accordingly, it is an object of the present invention to provide effective methods for detecting any faulty events in the manufacturing process of biochips or in experiments using biochips from the data obtained in the experiments using the biochips.

The present invention achieves the above object by displaying errors present in the data obtained from a biochip in a manner that is visually easy to interpret and quantifying such errors. Specifically, a plurality of sections is defined on a single biochip. The same type of control material is diluted to different concentrations and is spotted in a plurality of spots in each of the sections to serve as controls. A mixed sample is prepared by mixing two types of samples each labeled with a different fluorescent dye and is used in a hybridization reaction on the biochip. Upon completion of the hybridization reaction, the measurement data for two types of fluorescent signals emitted from the two types of the fluorescent dyes are plotted on a graph for each section. The graphs are displayed on a single screen in the same arrangement as that of the sections on the biochip for comparison. In order to give an idea of how the measured data for controls are dispersed, the experimental errors are quantified by examining the linearity of data points for each control or by examining a slope angle of a straight line fitted to data points, the data points in each case plotted on a graph with vertical and horizontal axes representing the intensities of fluorescent signals for respective fluorescent dyes.

In experiments using biochips, a discrepancy may arise between the observed intensities of fluorescent signals and the actual expression levels. The discrepancy may vary from one biochip to another, or from one section to another in a biochip, due to variations in the spotted amounts of materials on the biochip, variations in the amounts of elements such as DNA, RNA or cDNA contained in a spot, or variations in the hybridization reaction. In order to correct such discrepancies, controls are arranged on the biochip. A control may be a gene known as a housekeeping gene which is constantly expressed in various types of cells to provide the maintenance activities required by all cells. Other materials that can be used as a control include a gene that is incapable of being expressed, such as a gene exclusively expressed in plants and not in animals, or a fluorescent dye that do not have to do with genes. These materials are spotted on a biochip to serve as a standard for fluorescent signals. Controls are typically used as a standard for fluorescent signals to correct data while they are used to measure the extent of data dispersion in the present invention.

In the present invention, the measured data for controls are used to detect the experimental errors in biochip experiments. The data are plotted on a graph for each section, and the resulting graphs are simultaneously displayed on a single screen in the same arrangement as that of the sections on the biochip.

Two approaches are employed in the present invention in order to quantify the dispersion of the measured data for controls. One approach is based on the linearity of the measured data for controls. That is, a straight line that best fits to multiple plots, or data points, for controls with different concentrations, which are obtained through dilutions using different dilution factors, is determined on the assumption that the ratio of the signal intensities for one of the two types of fluorescent dyes to the signal intensities for the other fluorescent dye remains substantially constant irrespective of the concentrations of the controls. Then, the linearity is quantitatively evaluated by means of a standard known as the coefficient of determination to see if plots are close to the line. Quantification of errors is thus achieved by evaluating errors by determining the coefficient of determination for the fitted line. The other approach is based on slopes defined for each data points on a graph. That is, errors are quantified by determining slopes of the lines drawn from data points to the origin.

From these observations, it is possible to estimate at what stage in the process of biochip experiments faulty events have occurred while taking into account, for example, changes in the conditions in the manufacturing of the biochip or in experiments using the biochip. Possible causes of errors include variations in the amounts of spotted liquids due to environmental factors such as temperatures and humidity, non-uniformity of hybridization reactions, insufficient rinsing of biochips after hybridization, errors caused by improper scanning of a fluorescence detection device due to an inclined biochip substate during detection of fluorescent light from the spots, distorted biochip substrates, errors in scanning caused by dusts present in the ambient air or in solutions, fluorescence inherent to biochip substrates, noises caused by a photoelectron amplifier, and the like. By associating these potential causes with the values of the errors quantified in accordance with the present invention and by considering the results of the experiments which are conducted under the same conditions as the initial experiments, the estimation of causes of errors can be facilitated.

In one aspect, the present invention provides a method for displaying results of hybridization experiments using a biochip. The method includes the steps of providing a biochip having a spot region divided into a plurality of sections, wherein the same type of control material that has been diluted to different concentrations is spotted in multiple spots in each of the sections; performing a hybridization reaction using a mixed sample prepared by mixing two different types of samples, each of which has been labeled with each of two different fluorescent dyes so as to obtain, for each control, measurement data concerning the intensities of two different types of fluorescent signals emitted from the two fluorescent dyes; plotting the data on a graph for each section, wherein the vertical axis and horizontal axis each represent the signal intensities of each of the two types of fluorescent signals; and simultaneously displaying on a single screen all of the graphs, each representing the data for one of the sections, in such a manner that the graphs are arranged in the same arrangement as that of the sections on the biochip.

In another aspect, the present invention provides a further method for displaying results of hybridization experiments using a biochip. The method includes the steps of providing a biochip having a spot region divided into a plurality of sections, wherein the same type of control material that has been diluted to different concentrations is spotted in multiple spots in each of the sections; performing a hybridization reaction using a mixed sample prepared by mixing two different types of samples, each of which has been labeled with each of two different fluorescent dyes so as to obtain, for each control, measurement data concerning the intensities of two different types of fluorescent signals emitted from the two fluorescent dyes; plotting the data on a graph for each section, wherein the vertical axis and horizontal axis each represent the signal intensities of each of the two types of fluorescent signals; determining the coefficient of determination between each plot and a straight line fitted to the plots; and displaying the coefficient of determination for each section on a graph that corresponds to each section.

In a further aspect, the present invention provides a further method for displaying results of hybridization experiments using a biochip. The method includes the steps of providing a biochip having a spot region divided into a plurality of sections, wherein the same type of control material that has been diluted to different concentrations is spotted in multiple spots in each of the sections; performing a hybridization reaction using a mixed sample prepared by mixing two different types of samples, each of which has been labeled with each of two different fluorescent dyes so as to obtain, for each control, measurement data concerning the intensities of two different types of fluorescent signals emitted from the two fluorescent dyes; plotting the data on a graph for each section, wherein the vertical axis and horizontal axis each represent the signal intensities of each of the two types of fluorescent signals; determining maximum, minimum and average slope angles for a set of straight lines, each of which extends from each of the plots to the origin, the slope angle being defined between each of the straight lines and the horizontal axis; and displaying the maximum, minimum and average slope angles on a graph in such a manner that each set of angles corresponds to each section.

In a still further aspect, the present invention provides a method for evaluating errors in hybridization experiments using a biochip. The method includes the steps of providing a biochip having a spot region divided into a plurality of sections, wherein the same type of control material that has been diluted to different concentrations is spotted in multiple spots in each of the sections; performing a hybridization reaction using a mixed sample prepared by mixing two different types of samples, each of which has been labeled with each of two different fluorescent dyes so as to obtain, for each control, measurement data concerning the intensities of two different types of fluorescent signals emitted from the two fluorescent dyes; plotting the data on a graph for each section, wherein the vertical axis and horizontal axis each represent the signal intensities of each of the two types of fluorescent signals; determining the coefficient of determination between each plot and a straight line fitted to the plots; and evaluating experimental errors using the coefficient of determination.

In a still further aspect, the present invention provides a further method for evaluating errors in hybridization experiments using a biochip. The method includes the steps of providing a biochip having a spot region divided into a plurality of sections, wherein the same type of control material that has been diluted to different concentrations is spotted in multiple spots in each of the sections; performing a hybridization reaction using a mixed sample prepared by mixing two different types of samples, each of which has been labeled with each of two different fluorescent dyes so as to obtain, for each control, measurement data concerning the intensities of two different types of fluorescent signals emitted from the two fluorescent dyes; plotting the data on a graph for each section, wherein the vertical axis and horizontal axis each represent the signal intensities of each of the two types of fluorescent signals; determining slope angles for a set of straight lines, each of which extends from each of the plots to the origin, the slope angle being defined between each of the straight lines and the horizontal axis; and evaluating experimental errors using the slope angles.

Preferably, the slope angles are maximum, minimum and average slope angles of the slopes.

BRIEF DESCRIPTION OF THE DRAWINGS

These as well as other features of the present invention will become more apparent upon reference to the drawings in which:

FIG. 2 shows a specific example of gene expression data;

DETAILED DESCRIPTION OF THE PREFERRED EMBODIMENTS

Preferred embodiments of the present invention will now be described in detail by reference to the accompanying drawings.

Figure 1:
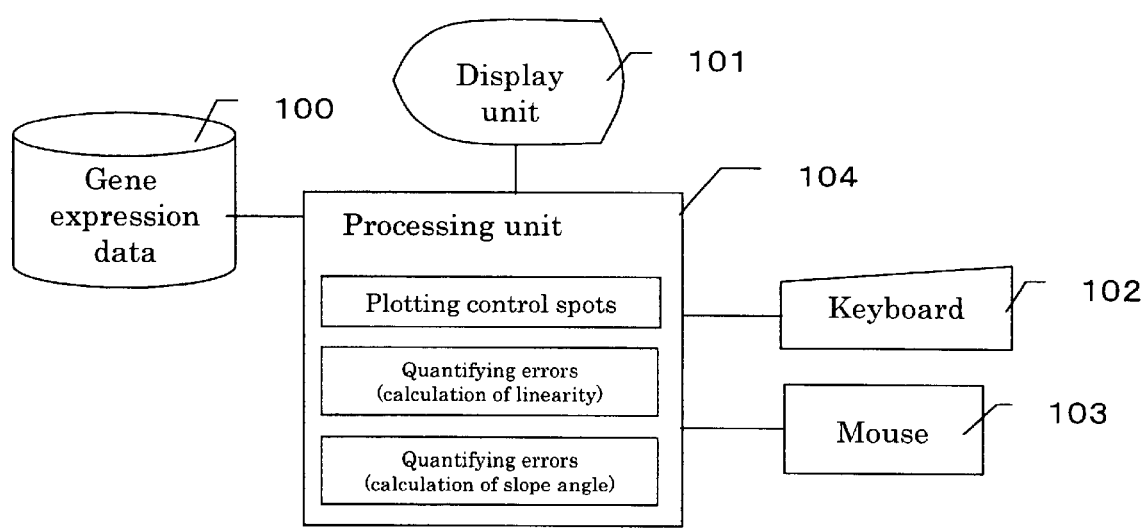
FIG. 1 schematically illustrates one example of a system configuration in accordance with the present invention.

FIG. 1 shows one example of a system configuration according to the present invention. The system comprises a storage unit 100 for storing gene expression data as numerical values representing the degree of gene expressions in a sequence of cellular processes, a display unit 101 for visualizing and displaying the expression data, input devices, such as a keyboard 102 and a mouse 103, for entering values into the present system or performing a selection, and a processing unit 104 for quantifying experimental errors based on the data values of controls. The processing unit 104 performs plotting of control spots on a graph and quantification of errors (i.e., calculation of the linearity and slopes.).

FIG. 2 shows a specific example of gene expression data stored in the storage unit 100. The data include experimental data obtained in an experiment in which diseased cells B are compared with normal cells A with respect to various genes. The results of the experiment, which are summarized in the table, represent the expression levels of genes (measurements of fluorescent signals from labeled cells) that are indexed by gene IDs. The s in the table can be interpreted as follows: for example, for the gene designated by gene ID No.1, the intensity of fluorescent signal was measured to be 1,234 for normal cells A whereas the measured intensity of the fluorescent signal was 56 for diseased cells B upon hybridization on a biochip. Though the total number of the subject genes used in an experiment may vary depending on experiments, currently available biochips are capable of handling several hundred to several tens of thousand genes.

Figure 3:
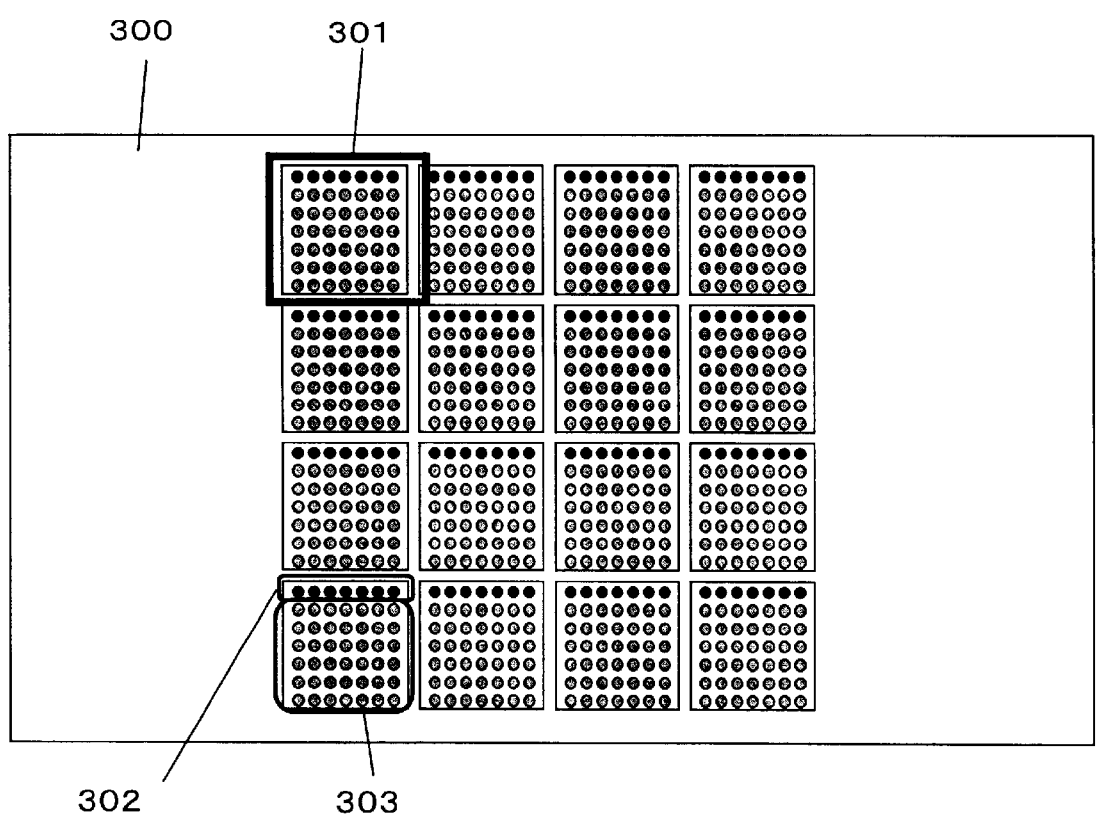
FIG. 3 schematically illustrates one example of spotting on a biochip in accordance with the present invention.

FIG. 3 is a schematic illustration showing one example of the biochip. A single biochip 300 is divided into a plurality of sections 301. In the example shown, the biochip 300 is divided into 16 sections in a 4×4 arrangement. Arranged in each section 301 are a plurality of control spots 302 that serve as controls and a plurality of element spots 303 for elements such as genes, DNA fragments, or RNA that are to hybridize to samples. The same control material is spotted on all of the control spots 302 on the same biochip 300. As described above, the control material may include housekeeping genes, genes incapable of being expressed, fluorescent dyes, and the like.

Figure 4:
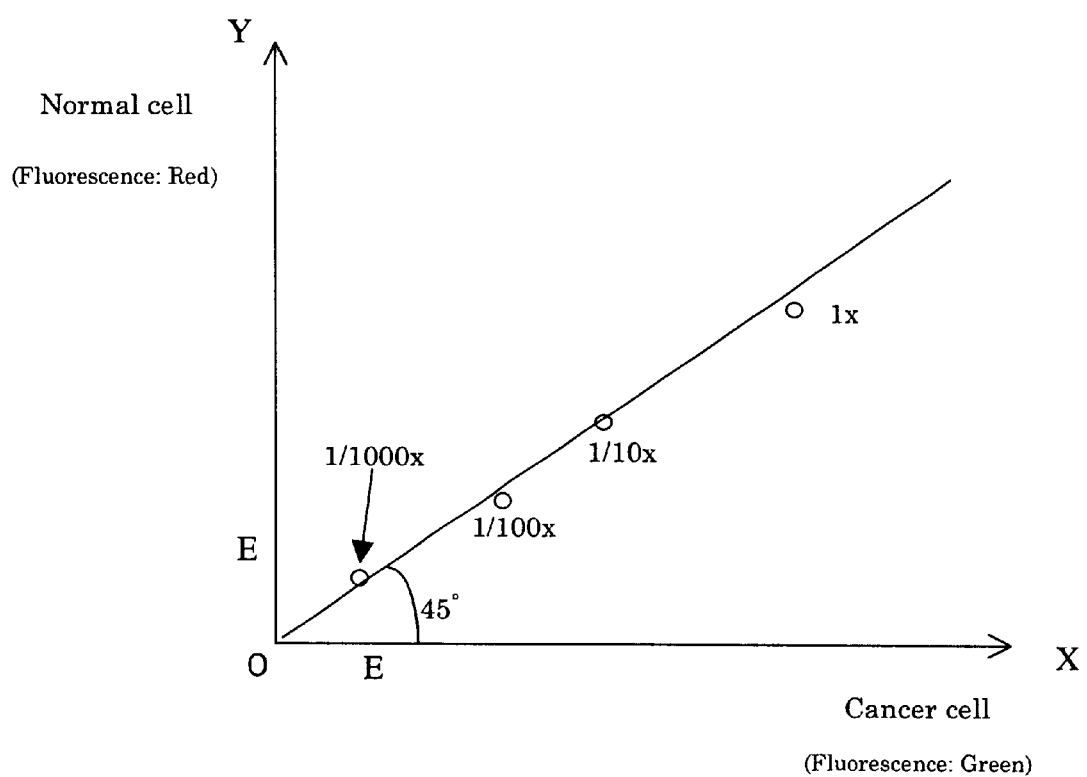
FIG. 4 shows one example of displaying typical control data.

Controls are prepared for spotting by diluting a stock solution to several different concentrations. In a graph shown in FIG. 4, data points for fluorescent signals are plotted so that each of the data points corresponds to one of the controls prepared in four different concentrations (namely, stock solution, 1:10 dilution, 1:100 dilution, and 1:1000 dilution). It is expected that the data points for the fluorescent signals be aligned on a straight line with a slope of 45° as shown in FIG. 4 in a spaced apart relationship that reflects the dilution factors since a known gene that is known to exhibit a constant expression level, whether or not the cell is normal, is used as control. The reason why this should be true is as follows: In the graph shown in FIG. 4, the Y-axis represents signal intensities of a fluorescent dye used to label normal cells while x-axis represents signal intensities of another fluorescent dye used to label cancer cells. Given this, the ratio of the signal intensities for one of the two fluorescent dyes to the signal intensities for the other fluorescent dye should remain constant since the gene serving as control is contained in the same amount in both of the two types of cells.

In a hybridization experiment, the biochip as shown in FIG. 3 is used. RNA is extracted from two different types of cells, for example, normal cells and cancer cells. The RNA samples are respectively labeled with two different fluorescent dyes, and equal amounts of the RNA samples are mixed together. The resulting RNA mixture is used as a sample for the experiment. Upon completion of hybridization, light is irradiated onto the biochip to excite the dyes, and the intensities of fluorescent signals that are emitted from the control spots and the element spots placed in each section of the biochip are measured. The measurements are stored as gene expression data.

Figure 5:
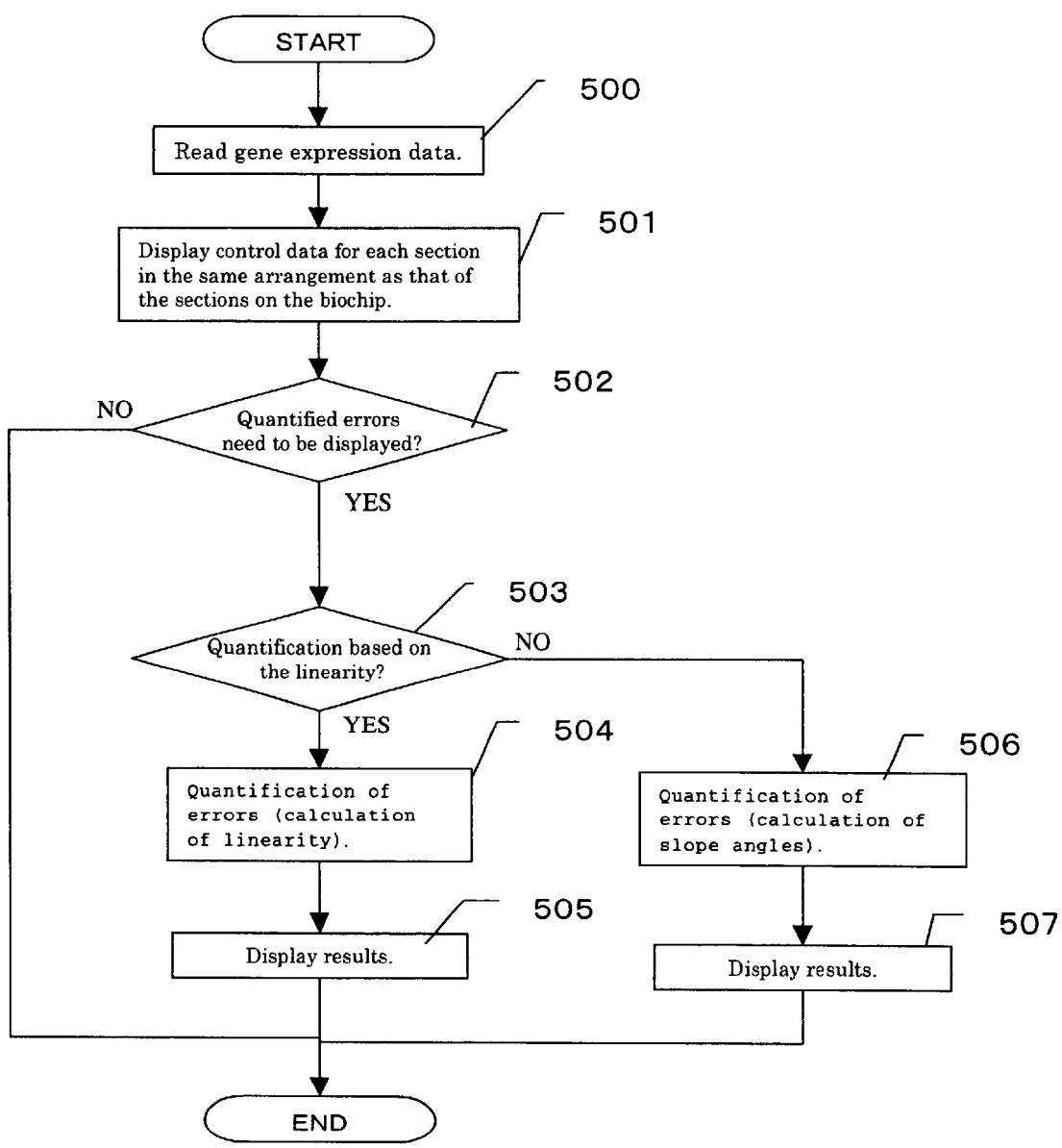
FIG. 5 is a flow chart showing a flow of processes in accordance with the present invention.

FIG. 5 is a flow chart schematically showing the flow of processes in one embodiment of methods for displaying the gene experiment data in accordance with the present invention. The processes are described one by one in the order appearing in the flow chart.

First, in step 500, gene expression data is read from the storage unit 100 into the processing unit 104 shown in FIG. 1. Next, in step 501, data for controls on the biochip are plotted on a graph for each of the sections. The graphs are displayed on a screen so that each graph corresponds to a respective section on the biochip.

Figure 6:
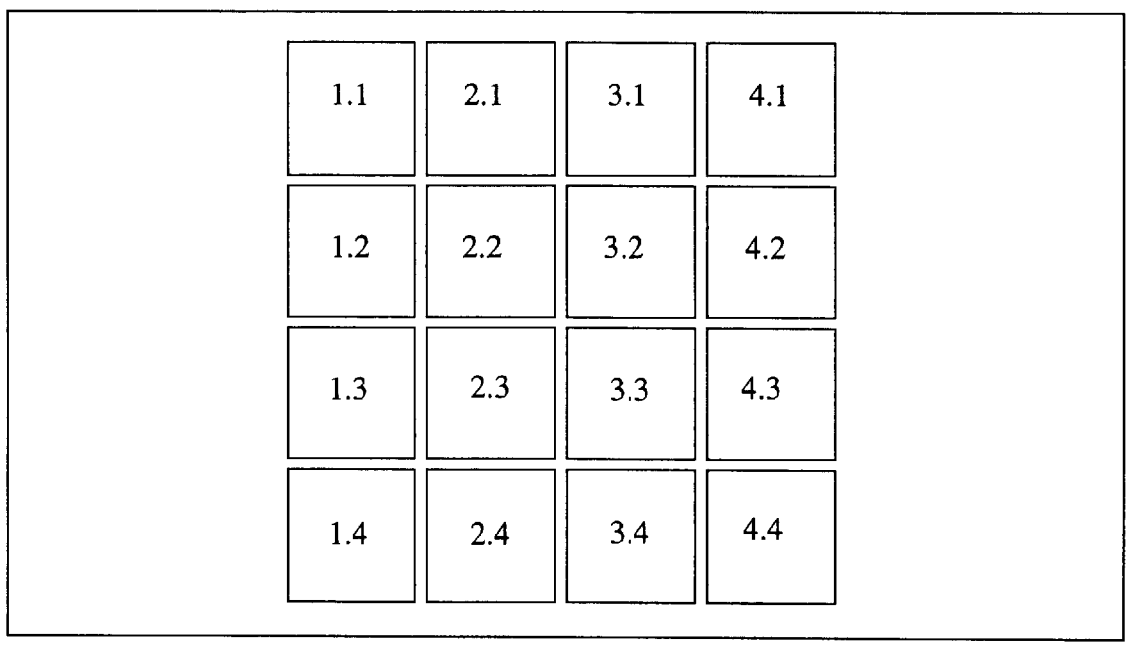
FIG. 6 shows one example of displaying sections on a biochip in accordance with the present invention.

For example, the biochip as shown in FIG. 3 is divided into 16 sections in a 4×4 arrangement with multiple control spots 302 being spotted in each section. The spotted controls are of the same type for all of the sections. To specify each section, section IDs are defined such that a section situated (a)th from the leftmost column and (b)th from the uppermost row is assigned a section ID (a,b), as shown in FIG. 6. For each section, the two different types of fluorescent signals are plotted on a graph with one axis representing the fluorescent signal intensities of one of the two fluorescent dyes that is used to label RNA extracted from normal cells and the other axis representing the fluorescent signal intensities of the other fluorescent dye used to label RNA extracted from cancer cells.

Figure 7:
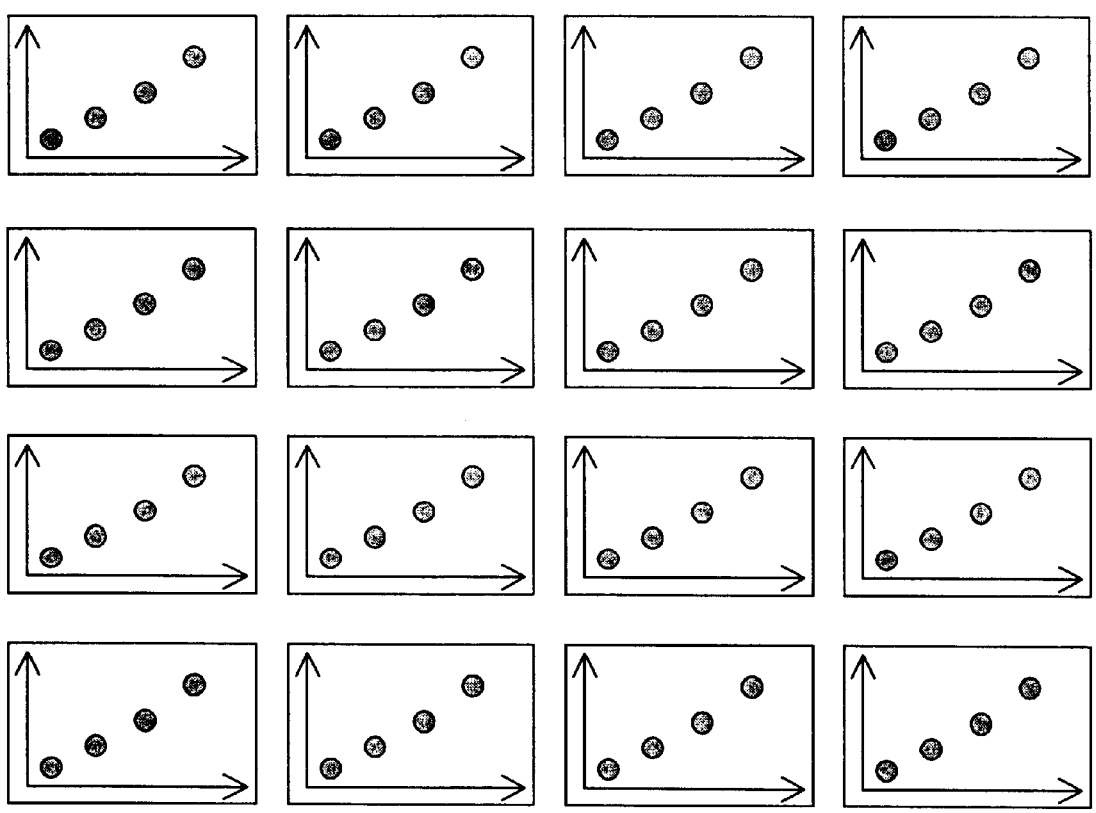
FIG. 7 shows one example of displaying data for controls for a single biochip in accordance with the present invention.
Figure 8:
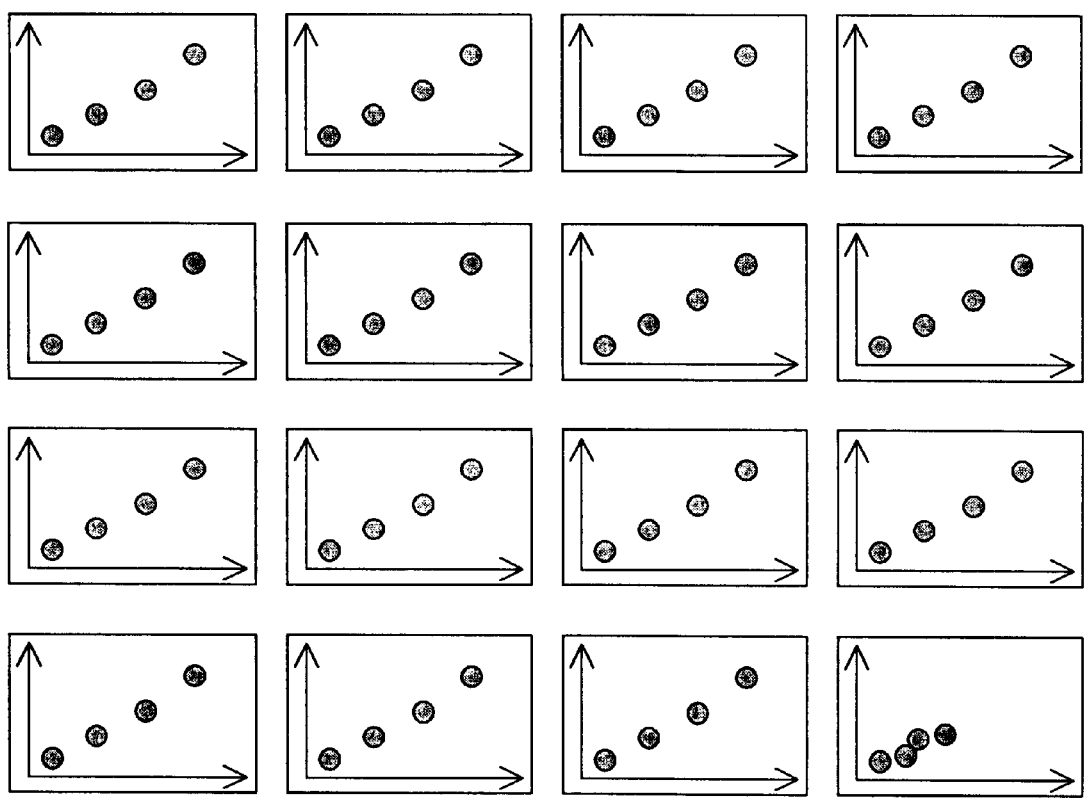
FIG. 8 shows one example of displaying data for controls for a single biochip in accordance with the present invention.

As shown in FIGS. 7 and 8, the graphs, each of which corresponds to one of the sections on the single biochip, are displayed on a single screen in the same arrangement as that of the sections on the biochip. This displaying scheme provides an effective way of visually recognizing what reactions are taking place in which section(s) on a biochip, thereby allowing the operator to skim the whole biochip to see the overall occurrences of experimental errors on the single biochip. For instance, as shown in FIG. 7, if similar graphs are obtained for all of the sections on a biochip in which the data plots are substantially aligned on a straight line with a slope of 45°, it can be inferred that the manufacture of the biochip has been substantially flawless and that uniform hybridization has been achieved for every section. In comparison, as shown in FIG. 8, if the results show different tendencies for a particular section(s) than the other sections on a biochip (in this case, the bottom section in the rightmost column), the implication is that some faulty events have taken place in regard of proper functioning of the biochip in the section (4, 4).

Referring again to FIG. 5, if errors are to be quantified for the displayed data (step 502 in FIG. 5), how the errors are quantified is selected (step 503 in FIG. 5).

If it has been determined that the errors are to be quantified based on the linearity, the process proceeds to step 504 and then to step 505. First, a straight line that best fits to multiple control plots for different concentrations obtained through dilutions with different dilution factors is determined by using the least-squares method on the assumption that the ratio of the signal intensities for one of the two types of fluorescent dyes to the signal intensities for the other fluorescent dye remains substantially constant irrespective of the concentrations of the controls. Then, the linearity is quantitatively evaluated by means of a standard known as the coefficient of determination to see if plots are close to the line. The least-squares method is a method in which a straight line, a curve, or a plane is fitted to data points plotted on a graph.

Figure 9:
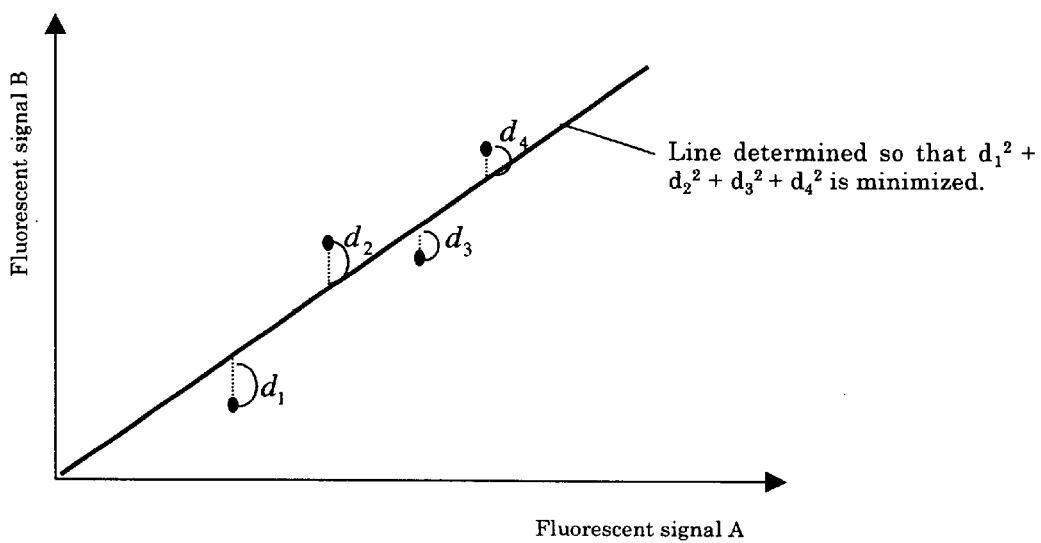
FIG. 9 is a graph explaining one method for quantifying errors with respect to the linearity of control data in accordance with the present invention.

Referring to FIG. 9, we now consider how to estimate values for the fluorescent dye B from the data for fluorescent dye A using the above-described curve fitting. Estimated data points are defined as the points on the fitted line at the intersections with vertical lines drawn from the actual data points. Provided this, the following relationship is obtained:

$$\sum_{i=1}^{n}(y_i - \overline{y})^2 = \sum_{i=1}^{n}(\overline{y}_i - \overline{y})^2 + \sum_{i=1}^{N}(y_i - \overline{y}_i)^2$$

where n is the total number of the data points, coordinates of the actual data points are given by $(x_i, y_i)$, (where i=1, 2, ..., n ), coordinates of the estimated data points are given by the following:

$(x_i, \overline{y}_i)$ (i=1, 2, ..., n), and the average values of $y_i$ (i=1, 2, ..., n) are given by the following:

$\overline{y}$ (total average).

The above equation means that the error, or deviation, of a measured value $(x_i, y_i)$ from the total average is given by the sum of a deviation of an estimated value $(x_i, \overline{y}_i)$ from the total average and a deviation of an observed value from the estimated value.

A quantity known as the coefficient of determination is generally introduced as a scale for evaluating the degree of fitness. The coefficient of determination is defined by the following equation:

$$R^2 = \frac{\sum_{i=1}^{n}(\overline{y}_i - \overline{y})^2}{\sum_{i=1}^{n}(y_i - \overline{y}_i)^2}$$

Note that $R^2$ is a value between 0 and 1, and the closer $R^2$ is to 1, the better the fitness.

The same principle applies to an approximation line that is used to estimate values for fluorescent signals A from the data for the fluorescent signals B. It is known that the coefficient of determination so defined equals to the coefficient of determination $R^2$ for an approximation line used to estimate the values of fluorescent signals B from the data for fluorescent signals A.

Figure 10:
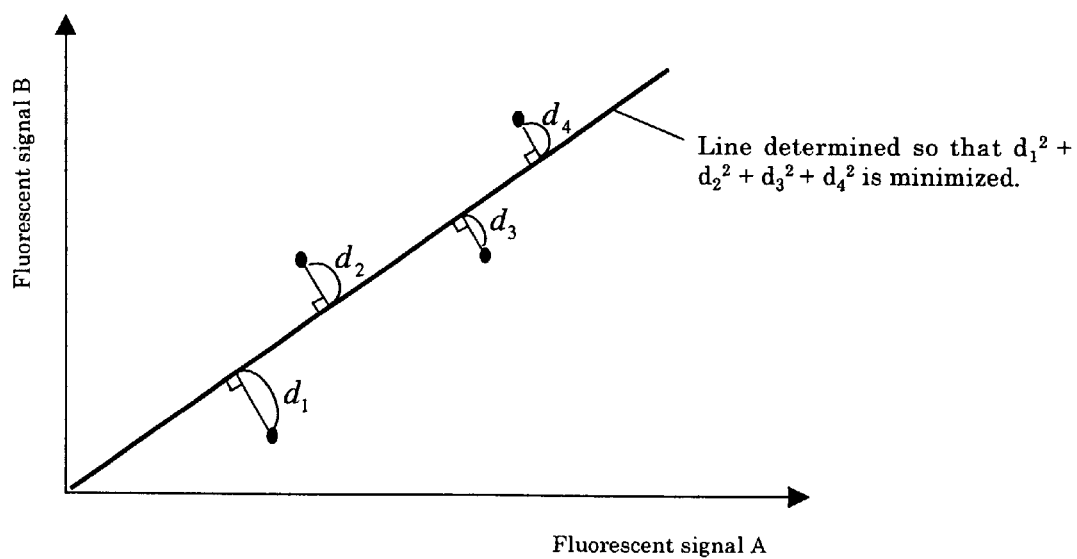
FIG. 10 is a graph explaining another method for quantifying errors with respect to the linearity of control data in accordance with the present invention.

While an example of curve fitting in which a straight line is fitted by means of the least-squares method has been described, there is another approach as shown in FIG. 10 in which a straight line is determined so that the sum of the lengths of lines drawn from each point perpendicularly to the fitted line is minimized. In this case, the coefficient of determination can also be defined in the same manner as in the case of the curve fitting using the least-squares method.

Figure 11A:
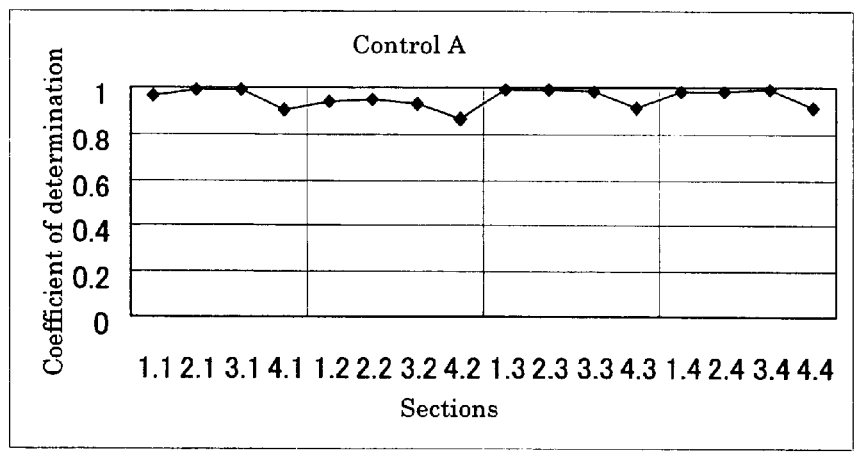
FIGS. 11A and 11B are graphs showing examples of displaying the results of the quantification of errors with respect to the linearity of control data, in accordance with the present invention.
Figure 11B:
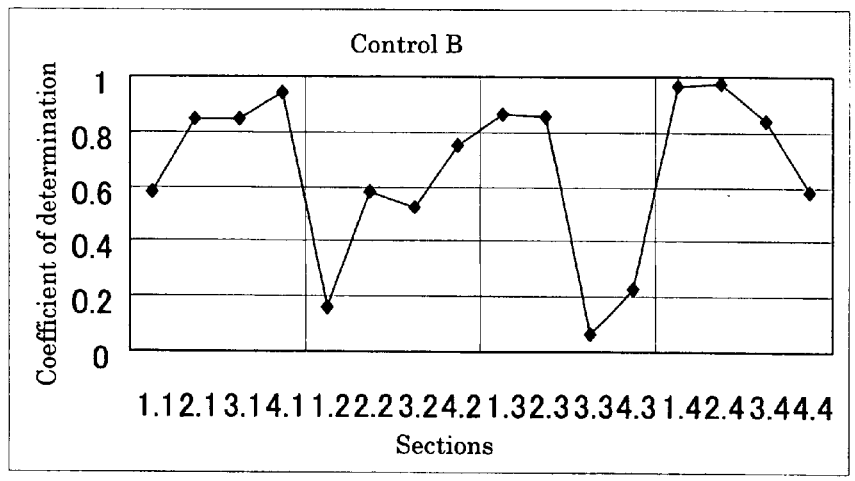

In FIGS. 11A and 11B, particular examples of showing the results of error quantification by means of the linearity are shown. In these graphs, the vertical axes represent the coefficient of the determination, and the horizontal axes represent section IDs, and the tendencies that the controls show are examined from one section to another. In the example of control A shown in FIG. 11A, the coefficient of the determination is close to 1 in every section, suggesting that when the data points corresponding to the controls with different concentrations are plotted on a graph, the points are substantially aligned on a straight line. In comparison, in the example of control B shown in FIG. 11B, there are significant deviations of the coefficient of determination among the sections. This indicates that the ratio of the intensities of the fluorescent signal A to the intensities of the fluorescent signal B varies significantly.

On the other hand, when errors are to be quantified with respect to slope angles, the process proceeds to step 506 and then to step 507 as seen in FIG. 5. When the data points for controls with different concentrations are plotted on a graph, and provided that the materials are the same for all of the controls, the ratio of the intensities of the fluorescent signals A to those of the fluorescent signals B should remain substantially constant and points for each control must be substantially aligned on a straight line with a slope of 45°. To demonstrate this, measured data for multiple controls with different concentrations are plotted on a graph as shown in FIG. 12, for each section of a biochip (shown in the is the case in which four controls are used), and maximum, minimum and average slope angles are determined for the data points relative to the origin.

Figure 13A:
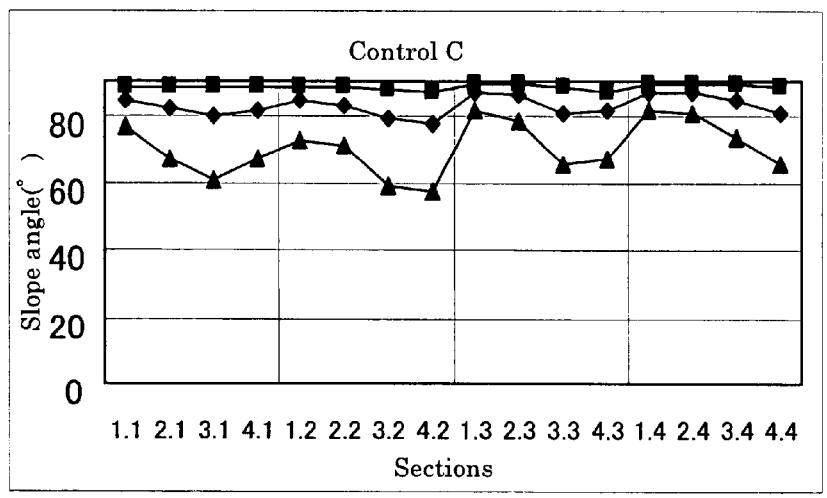
FIGS. 13A and 13B are graphs showing examples of displaying the results of the quantification of errors with respect to slope angles defined for control data, in accordance with the present invention.
Figure 13B:
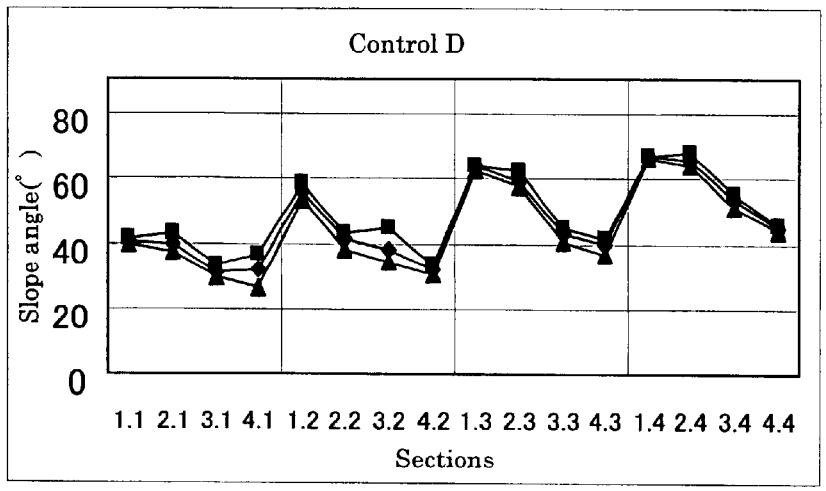

In FIGS. 13A and 13B, particular examples of showing the results of error quantification by means of slope angles are shown. In graphs shown in FIG. 13, the vertical axes represent slope angles and the horizontal axes represent section IDs, and the tendencies that the controls show from one section to another are shown. As can be seen in the example of control C shown in FIG. 13A, the discrepancy between the maximum slope angle and the minimum slope angle is considerably large in every section. This indicates that the ratio of the intensities of one of the two types of fluorescent signals emitted from the controls to the intensities of the other type of fluorescent signals varies significantly. In comparison, in the example of control D as shown in FIG. 13B, the discrepancy between the maximum slope and minimum slope is relatively small in every section, indicating that the ratio of the intensities of one of the two types of fluorescent signal emitted from the controls to the intensities of the other type of fluorescent signal is substantially constant. It can also be seen from the graph that the slope angles tend to increase from the right to the left sections and from the top to the bottom sections.

Users of the biochip can determine where in the experimental process an error(s) has occurred based on these displays showing the quantified linearity or slope angles that are defined by plotting the measured data of the controls on a graph. For example, the result as shown in FIG. 13B may be implying the possibility that the biochip was inclined during scanning, which could cause the detected intensities of one of the two types of the fluorescent signals to become increasingly higher than their actual values in the direction toward the lower left section and the intensities for the other type of fluorescent signals to become increasingly higher than their actual values in the direction toward the upper right section, resulting in greater deviations in the slope angles. This suggests that, although the spotting has been accurately done on the biochip, the measured values have deviated due to the physical differences in the positions from which the fluorescent lights were measured.

Figure 12:
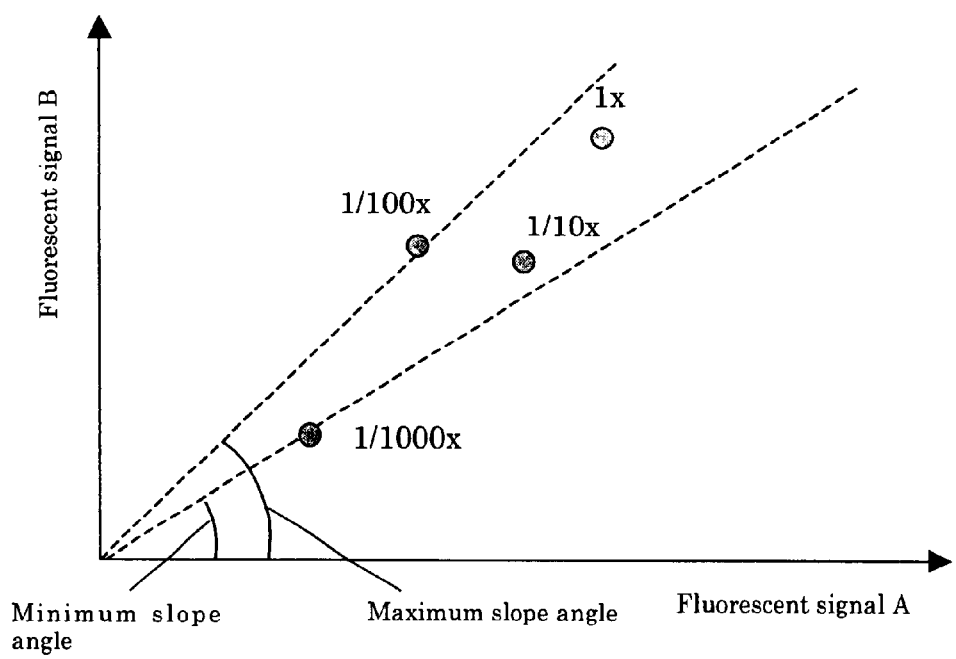
FIG. 12 is a graph explaining one example of quantification with respect to slope angles defined for control data, in accordance with the present invention.

Referring now to FIG. 12 which shows an example of a scattered plot, it can be seen that the measured data for controls are significantly dispersed so that the points on the graph show relatively low linearity and there is a considerably large difference between the maximum slope angle and the minimum slope angle. In comparison, in an example shown in FIG. 14, the data for controls are substantially aligned on a straight line, showing a high linearity. Also, the relatively small difference between the maximum slope angle and the minimum slope angle indicates that the ratio of the intensities of one of the two types of fluorescent signals to those of the other type of fluorescent signal remains substantially constant. It is noted that the whole line is shifted from the 45° line toward the vertical axis. Thus, it is possible to accurately evaluate conditions associated with controls by considering both the linearity and slope angles.

Figure 14:
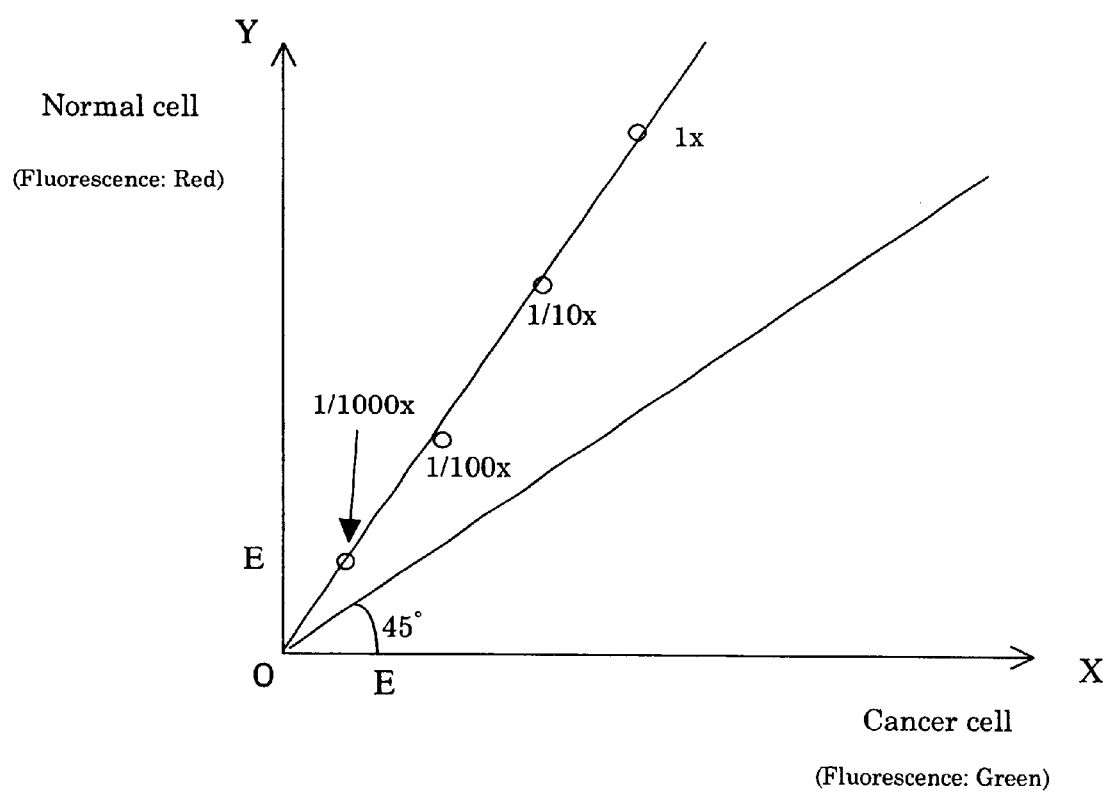
FIG. 14 is a graph showing one example of displaying the manner of quantification with respect to slope angles to all of the control data in accordance with the present invention.

As has been described, the present method makes it possible to skim the whole biochip to find experimental errors by simultaneously displaying on a single screen all the results of the measurements of controls, which are of the same type and are spotted in each section of the biochip as shown in FIG. 3, in such a manner that the data for each section correspond to respective sections on the biochip, as shown in FIGS. 7 and 8. Quantification of the experimental errors is also achieved by examining the linearity of the data points plotted on a graph as shown in FIGS. 9 and 10, and examining slope angles defined for respective points plotted on a graph as shown in FIGS. 12 and 14 for the measurement of how the data for controls are dispersed.

Figure 15:
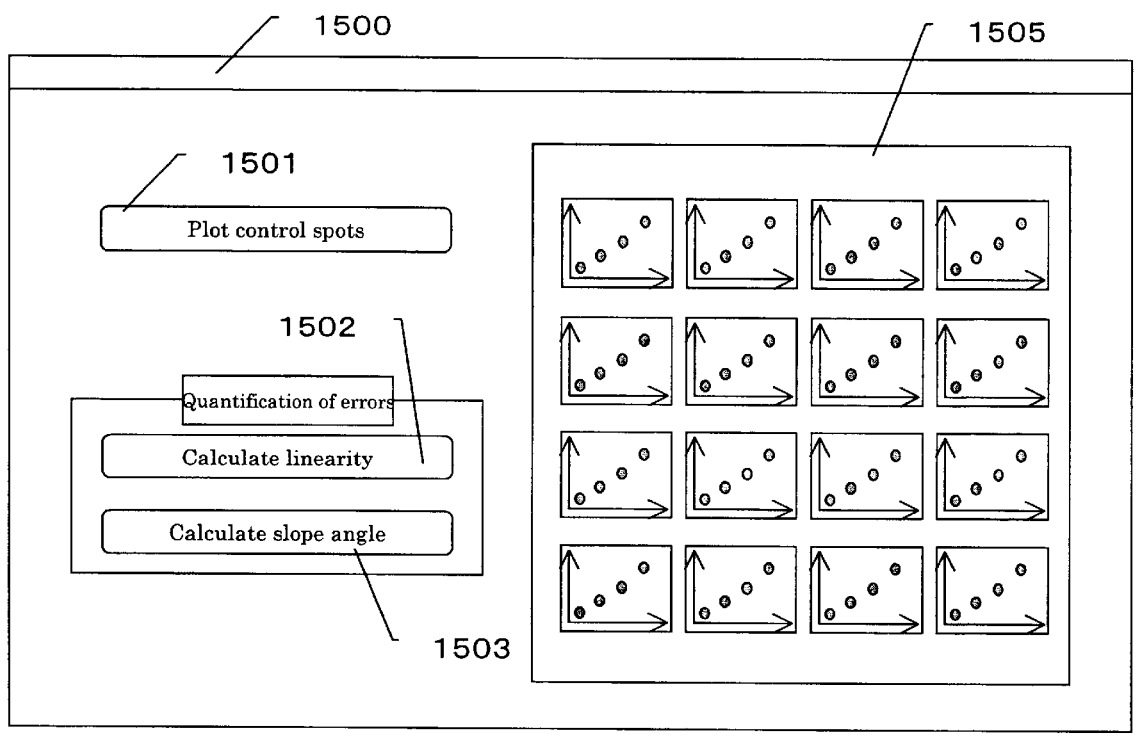
FIG. 15 illustrates one example of an interface in accordance with the present invention for displaying control data together with the results of the quantification of errors with respect to the linearity of the control data and with respect to the slope angles defined for the control data for a single biochip.
Figure 15:
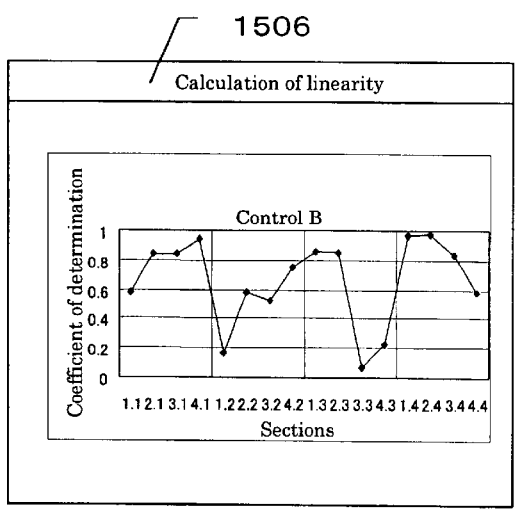
Figure 15:
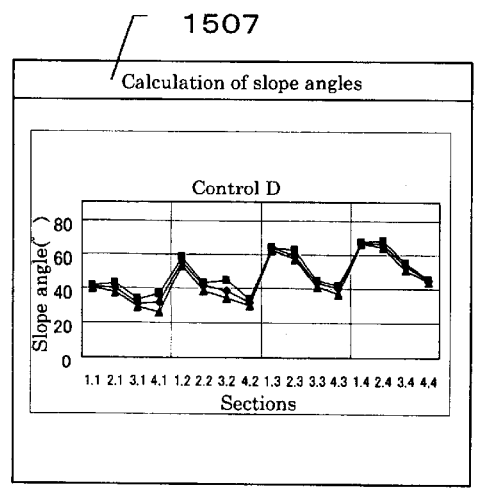
Figure 16:
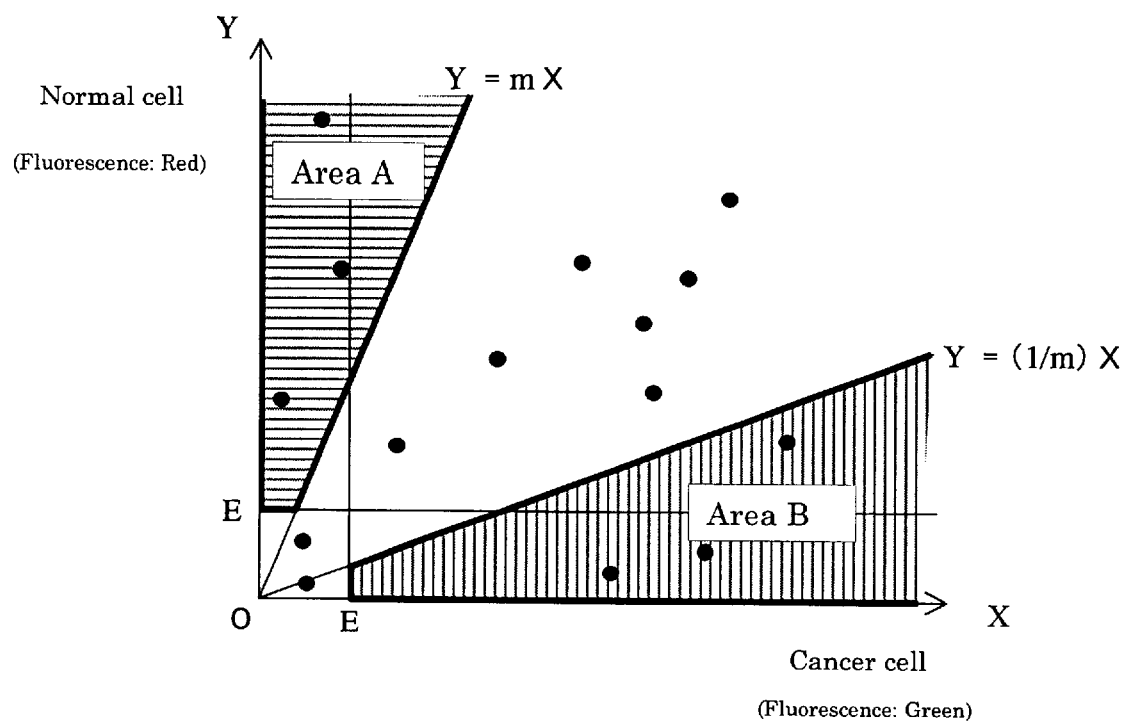
FIG. 16 shows one example of displaying typical results of an analysis of gene expression data.
Figure 17:
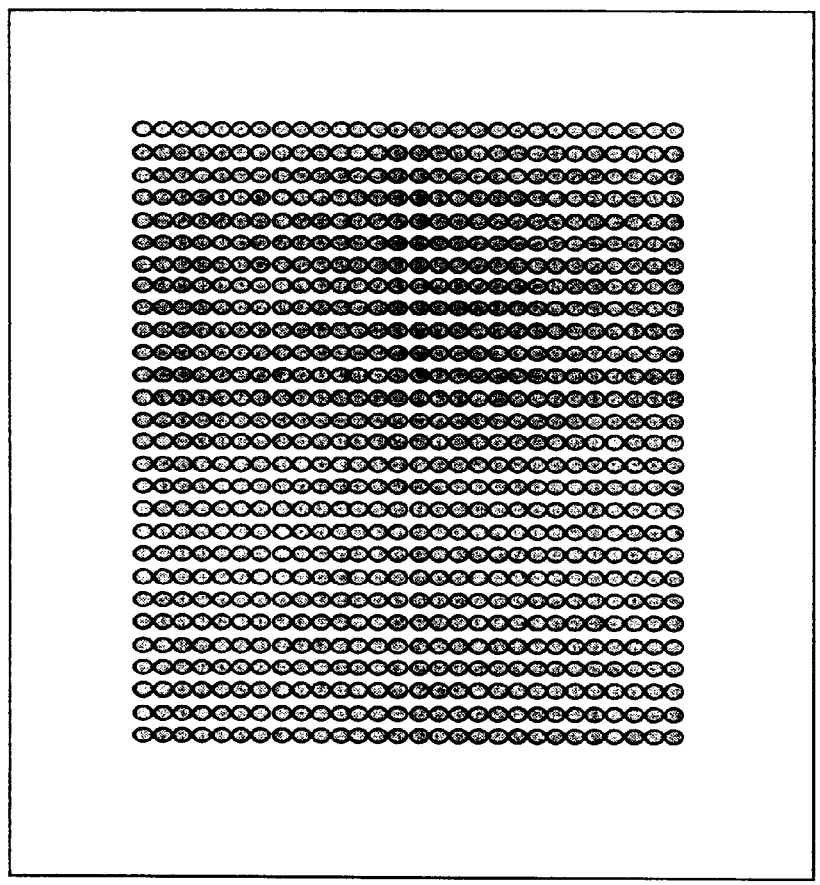
FIG. 17 shows one example of an image of a biochip read by a scanner.

In implementing the processes, an interface such as that shown in FIG. 15 may be useful for facilitating the operation. The interface in FIG. 15 includes a plurality of buttons to help implement the above-described three processes; buttons 1501, 1502 and 1503 on a window 1500 displayed in the display unit are assigned to execute the processes of plotting the data for controls for all of the sections, calculating the linearity used in the quantification of errors, and calculating slope angles used in the quantification of errors, respectively.

First, the button 1501 is clicked on by means of a pointing device such as a mouse. This causes a plurality of scattered plots, each of which corresponds to one of the sections on a biochip as shown in FIG. 7, to be displayed in a display frame 1505 on the window 1500. Next, with respect to the buttons for the quantification of errors, the button 1502 is clicked on to calculate the above-described linearity. This causes a fitted line to be displayed for each section in the display frame 1505. In addition, a graph such as that shown in FIG. 11B is displayed in a window 1506 in which the vertical axis represents the coefficient of determination and the horizontal axis represents section IDs. By clicking on the button 1503, slope angles are calculated in the manner described above, and a graph is displayed in a window 1507 in which the vertical axis represents the slope angles in degrees and the horizontal axis represents section IDs.

The method for displaying the results of biochip experiments or the method for evaluating the errors in biochip experiments according to the present invention may be implemented by a computer. This can be achieved by storing a program that executes the above processes in a storage medium and reading the program from the storage medium into a computer.

Accordingly, the present invention allows the experimental data obtained from a biochip to be displayed in a manner that is visually easy to interpret and thereby helps estimate at what stage in the experimental process faulty events have occurred. Furthermore, the present invention allows the quantification of experimental errors by analyzing the resulting graphs with respect to the linearity and slope angles.

It should be appreciated by those of ordinary skill in the art that modifications and alterations may be made to the present invention without departing from the spirit and scope the invention. Thus, the true scope of the invention is to be construed by the language that defines the appended claims.

What is claimed is:

1. A method for displaying results of hybridization experiments using a biochip, the method comprising the steps of:

providing a biochip having a spot region divided into a plurality of sections, wherein the same type of control material that has been diluted to different concentrations is spotted in multiple spots in each of the sections;

performing a hybridization reaction using a mixed sample prepared by mixing two different types of samples, each of which has been labeled with each of two different fluorescent dyes so as to obtain, for each control, measurement data concerning the intensities of two different types of fluorescent signals emitted from the two fluorescent dyes;

plotting the data on a graph for each section, wherein the vertical axis and horizontal axis each represent the signal intensities of each of the two types of fluorescent signals; and simultaneously displaying on a single screen all of the graphs, each representing the data for one of the sections, in such a manner that the graphs are arranged in the same arrangement as that of the sections on the biochip.

2. A method for displaying results of hybridization experiments using a biochip, the method comprising the steps of:

providing a biochip having a spot region divided into a plurality of sections, wherein the same type of control material that has been diluted to different concentrations is spotted in multiple spots in each of the sections;

performing a hybridization reaction using a mixed sample prepared by mixing two different types of samples, each of which has been labeled with each of two different fluorescent dyes so as to obtain, for each control, measurement data concerning the intensities of two different types of fluorescent signals emitted from the two fluorescent dyes;

plotting the data on a graph for each section, wherein the vertical axis and horizontal axis each represent the signal intensities of each of the two types of fluorescent signals;

determining a coefficient of determination between each plot and a straight line fitted to the plots; and displaying the coefficient of determination for each section on a graph that corresponds to each section.

3. A method for displaying results of hybridization experiments using a biochip, the method comprising the steps of:

providing a biochip having a spot region divided into a plurality of sections, wherein the same type of control material that has been diluted to different concentrations is spotted in multiple spots in each of the sections;

performing a hybridization reaction using a mixed sample prepared by mixing two different types of samples, each of which has been labeled with each of two different fluorescent dyes so as to obtain, for each control, measurement data concerning the intensities of two different types of fluorescent signals emitted from the two fluorescent dyes;

plotting the data on a graph for each section, wherein the vertical axis and horizontal axis each represent the signal intensities of each of the two types of fluorescent signals;

determining maximum, minimum and average slope angles for a set of straight lines, each of which extends from each of the plots to the origin, the slope angle being defined between each of the straight lines and the horizontal axis; and displaying the maximum, minimum and average slope angles on a graph in such a manner that each set of angles corresponds to each section.

4. A method for evaluating errors in hybridization experiments using a biochip, the method comprising the steps of:

providing a biochip having a spot region divided into a plurality of sections, wherein the same type of control material that has been diluted to different concentrations is spotted in multiple spots in each of the sections;

performing a hybridization reaction using a mixed sample prepared by mixing two different types of samples, each of which has been labeled with each of two different fluorescent dyes so as to obtain, for each control, measurement data concerning the intensities of two different types of fluorescent signals emitted from the two fluorescent dyes;

plotting the data on a graph for each section, wherein the vertical axis and horizontal axis each represent the signal intensities of each of the two types of fluorescent signals;

determining a coefficient of determination between each plot and a straight line fitted to the plots; and evaluating experimental errors using the coefficient of determination.

5. A method for evaluating errors in hybridization experiments using a biochip, the method comprising the steps of:

providing a biochip having a spot region divided into a plurality of sections, wherein the same type of control material that has been diluted to different concentrations is spotted in multiple spots in each of the sections;

performing a hybridization reaction using a mixed sample prepared by mixing two different types of samples, each of which has been labeled with each of two different fluorescent dyes so as to obtain, for each control, measurement data concerning the intensities of two different types of fluorescent signals emitted from the two fluorescent dyes;

plotting the data on a graph for each section, wherein the vertical axis and horizontal axis each represent the signal intensities of each of the two types of fluorescent signals;

determining slope angles for a set of straight lines, each of which extends from each of the plots to the origin, the slope angle being defined between each of the straight lines and the horizontal axis; and evaluating experimental errors using the slope angles.

6. The method according to claim 5, wherein maximum, minimum and average slope angles are used to evaluate the experimental errors.

* * * * *